United States Patent [19]

Donovan

[11] Patent Number: 5,093,040
[45] Date of Patent: Mar. 3, 1992

[54] COMPLEX N-HYDROXYIMIDE COMPOUNDS AND THEIR USE AS DETERGENT ADDITIVES

[75] Inventor: Stephen F. Donovan, Fairfield, Conn.

[73] Assignee: American Cyanamid Company, Stamford, Conn.

[21] Appl. No.: 84,240

[22] Filed: Aug. 12, 1987

[51] Int. Cl.$^5$ ............................................. C11D 1/18
[52] U.S. Cl. .................................. 252/542; 252/524; 252/541; 562/565; 548/570; 548/542
[58] Field of Search ............... 562/565; 548/520, 542; 252/541, 542, 524

[56] References Cited

U.S. PATENT DOCUMENTS 2,974,944  2/1961  Chow et al. ..................... 562/565

Primary Examiner—Bruce Gray
Attorney, Agent, or Firm—Frank M. Van Riet

[57] ABSTRACT

Complex N-hydroxyimide compounds and carboxy hydroxamic acid-functional derivatives thereof are prepared from organic amines reacted with maleate esters and maleic anhydride. The compounds exhibit strong metal ion chelating properties and are useful as detergent additives to improve stain removal.

18 Claims, No Drawings

COMPLEX N-HYDROXYIMIDE COMPOUNDS AND THEIR USE AS DETERGENT ADDITIVES

The present invention relates novel N-hydroxyimide compounds exhibiting strong metal cation chelating properties, which can be used, e.g., to enhance the stain removing power of detergent compositions, particularly fabric-washing detergent compositions. In particular it relates to complex N-hydroxyimide compounds useful as detergent additives and to detergent compositions comprising at least one detersive surfactant and an effective amount of such N-hydroxyimide compounds.

BACKGROUND OF THE INVENTION

Detergent compositions have long employed materials, known as "builders", to improve the detergency of soaps and synthetic detergents by actively chelating alkali metal cations which are normal components of "hard" tap water. Such builders have been found to affect, for instance, soil suspension, emulsification of soil particles, solubilization of water-insolubles, and inactivation of various mineral constituents present in a detergent system. Many materials useful as builders have been proposed, and there effects are known. See, e.g., U.S. Pat. Nos. 3,852,213, 3,950,260, 4,182,718, and 4,440,646 (all incorporated herein by reference).

Recently, however, the attention of detergent manufacturers and researchers has turned to the role of heavier metal cations, i.e., transition metal cations and particularly iron, in the formation of stain complexes on fabrics and other surfaces. It has been observed that these multivalent transition metal cations, particularly iron ($Fe^{+++}$), enhance the binding of the components of many stains to substrates, and breaking up the cation-enhanced bonds is an effective approach to stain removal. Therefore, there is a strong need for the discovery of new materials that are effective as chelating agents for transition metal cations, are easy to prepare, and can be added to detergent compositions in economical amounts to boost stain-removing power.

It has now been discovered that complex N-hydroxyimide compounds derived from organic amine compounds and maleic acid esters are active transition metal ion chelants, particularly with respect to iron ($Fe^{+++}$). The N-hydroxyimides of the present invention are water-soluble and are active in stain removal.

SUMMARY OF THE INVENTION

It is therefore an object of the present invention to provide a new class of compounds which are strong metal ion chelating agents.

It is a further object of the present invention to provide new compounds useful as detergent additives for stain removal.

It is a further object of the present invention to provide novel detergent compositions.

It is a further object of the present invention to provide a fabric-washing detergent composition that is effective in stain removal.

It is a further object of the present invention to provide a method for preparing complex N-hydroxyimide chelating agents.

These and other objects are achieved, according to the present invention, by compounds of the formula

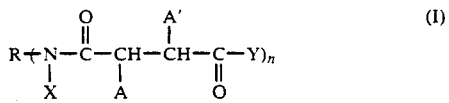

wherein
X is

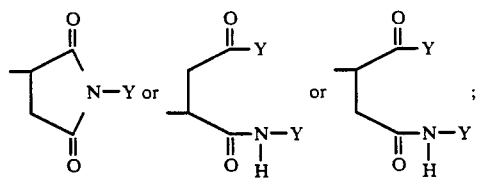

Y is hydroxyl or $-O^-M^+$, where $M^+$ an alkali metal cation (e.g., $Na^+$, $K^+$, $Li^+$, etc.) or ammonium ($NH_4^+$);
one of A and A' is hydrogen and the other is

R is an organic radical of 2-20 carbon atoms; and n is an integer equal to the valency of R.

Also contemplated herein are detergent compositions comprising one or more detersive surfactants and one or more detergent additives consisting essentially of N-hydroxyimide compounds of the formula

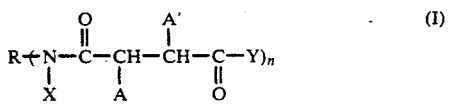

wherein
X is

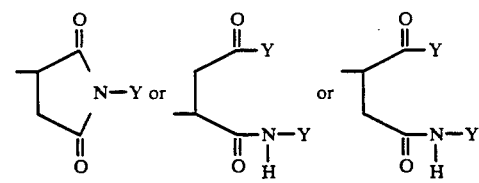

Y is hydroxyl or $-O^-M^+$, where $M^+$ is an alkali metal or ammonium cation;
one of A and A' is hydrogen and the other is

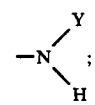

R is an organic radical of 2-20 carbon atoms; and n is an integer equal to the valency of R.

A method for preparing the complex N-hydroxyimide compounds according to the present invention is also contemplated.

DETAILED DESCRIPTION OF THE INVENTION

The complex H-hydroxyimide compounds of the present invention may be advantageously prepared from dialkyl maleate esters and organic amine compounds, preferably organic diamines having the general formula $H_2N-R-NH$, wherein R is a divalent organic radical of from 2-20 carbon atoms. The organic amine/polymaleate reaction products are further reacted with maleic anhydride to obtain tertiary amine compounds having maleic anhydride substituents as well as maleate ester substituents. These tertiary amine compounds are further reacted with hydroxylamine ($H_2NOH$) to obtain N-hydroxyimide compounds according to the present invention. The N-hydroxyimide compounds may be further reacted with a base to provide poly(carboxy hydroxamic acid) compounds. The latter N-hydroxyimide and poly(carboxy hydroxamic acid) products are water-soluble and exhibit strong metal ion chelating properties.

While the precise chemistry of the present detergent builders is not completely understood, it is believed that on treatment with base, ring opening reactions occur on the N-hydroxyimide molecule, adding carboxylic acid and hydroxyamic acid functions to the compound. Thus, a typical reaction scheme for the preparation of the compounds contemplated by the present invention is as follows:

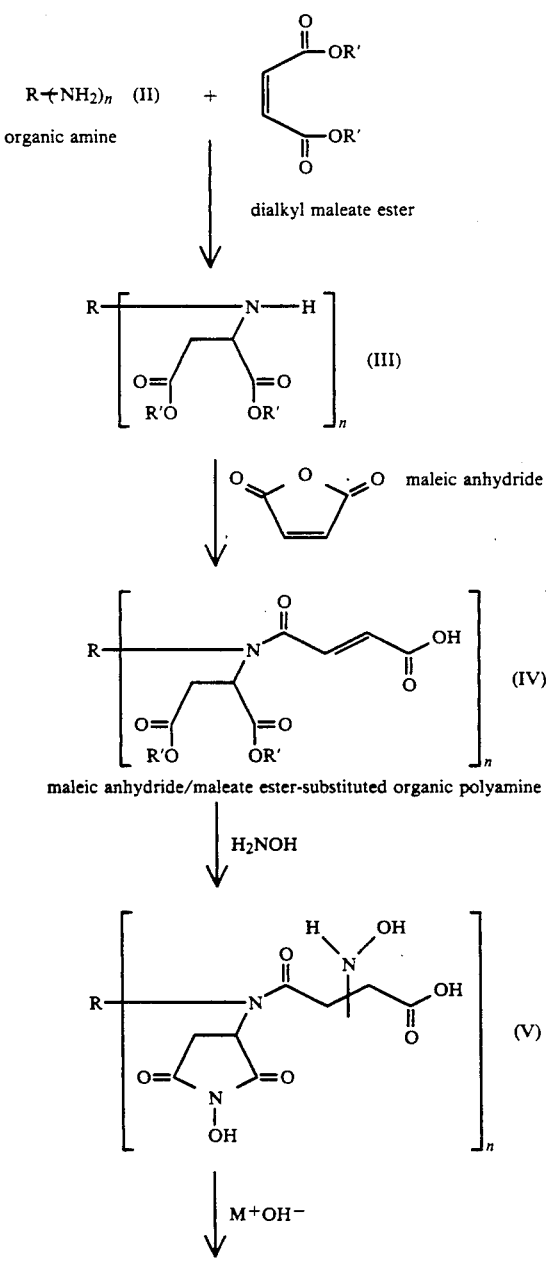

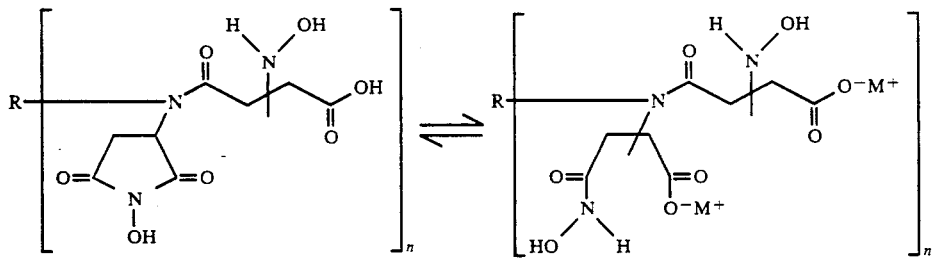

The organic amine starting materials suitable for use in the present invention are organic compounds having from 2 to about 20 carbon atoms and at least one amino substituent group. Diamines, for example, will have the general formula $H_2N$—R—$NH_2$, in which the two amino groups are bridged by a divalent organic radical having 2-20 carbon atoms, which divalent organic radicals include, e.g., aliphatic, alicyclic and aryl radicals such as straight chain or branched alkylene, alkenylene, cycloalkylene, arylene, alkarylene, and the like, and also divalent hetero radicals including hydrocarbon chains interrupted by one or more atoms of oxygen, nitrogen or sulfur and saturated or unsaturated divalent cyclic radicals containing one or more atoms of oxygen, nitrogen or sulfur.

Examples of diamines contemplated herein include ethylenediamine, trimethylenediamine, propylenediamine, tetramethylenediamine, t-butylenediamine, pentamethylenediamine, hexamethylenediamine, o-, m- and p-phenylenediamine, biphenylenediamine, naphthylenediamine, styrenediamine, xylylenediamine, etc.

Organic mono-amines are also suitable. These compounds will have the formula R—$NH_2$, in which R is a monovalent organic radical of 2-20 carbon atoms. Such radicals will include, e.g., aliphatic, alicyclic and aryl radicals such as straight chain or branched alkyl, alkenyl, cycloalkyl, aryl, alkaryl radicals, and the like, and also hetero radicals including hydrocarbon chains interrupted by one or more atoms of oxygen, nitrogen or sulfur and saturated or unsaturated cyclic radicals containing one or more atoms of oxygen, nitrogen or sulfur.

Preferred among organic mono-amines will be those in which R is a long, straight-chain saturated hydrocarbon radical. That is, in mono-amines of the formula R—$NH_2$, R will preferably be —$(CH_2)_{8-19}CH_3$, most preferably —$(CH_2)_{12-19}CH_3$. Special mention is made of the organic mono-amine, $H_2N$—$(CH_2)_{17}$—$CH_3$.

Also contemplated are more complex organic polyamines such as triamines, $R(NH_2)_3$; tetraamines, $R(NH_2)_4$; pentaamines, $R(NH_2)_5$, and the like, in which 3, 4, 5 or more amino groups, respectively, are bridged by trivalent, tetravalent, pentavalent, etc. organic radicals of 2-20 carbon atoms. The chemical structure of the organic radicals, e.g., in terms of chain length degree of branching, degree of unsaturation, steric hindrance, and other structural properties will affect the flexibility of the final product and the spacing between chelating groups, which, in turn, affects the chelating efficiency and the types of cations which are strongly sequestered by the final compound. Therefore, in practice, it may be possible by judicious selection of starting materials to tailor to some extent the detergent additives of the present invention to a particular detersive system or to work upon a particular type of stain complex. For the fabric-washing detergent systems contemplated in the present invention, diamine starting materials will be preferred. Substantially linear alkylenediamines are most preferred, especially those having the general formula $H_2N$—$(CH_2)_m$—$NH_2$, where m is 5 or more. Hexamethylenediamine is most preferred.

The organic amine is reacted with a dialkyl maleate ester of the formula R'OOC—CH=CH—COOR', where R' is lower ($C_1$-$C_6$) alkyl. Examples include dimethyl maleate, diethyl maleate dipropyl maleate, diisopropyl maleate, di-t-butyl maleate, etc. Dimethyl maleate is preferred.

The maleate ester is reacted with the organic amine in a suitable solvent. Toluene is preferred. Approximately 1 amine equivalent of the dialkyl maleate ester will be used, since a secondary amine reaction product is desired. Thus, where an organic diamine is used, preferably about 2-2.5 moles of a dialkyl maleate ester will be used, per mole of the diamine compound, in order to obtain an N,N'-substituted organic diamine intermediate. (See Formula III, supra, where n=2.)

The maleate ester-substituted organic amine is further reacted, in accordance with the invention, with maleic anhydride. Typically, the maleic anhydride is added to the dialkyl maleate ester/organic amine reaction mixture, after allowing sufficient time for the initial ester substitution (producing the secondary amine intermediate) to be substantially completed. Preferably, approximately 1 amine equivalent of maleic anhdyride will be used for this reaction as well, although use of excess amounts is also contemplated in order to ensure complete reaction of free amine moieties or to speed the rate of reaction. Most preferably, in the case where diamine starting materials are used, about 2-3 moles of maleic anhydride, per mole of maleate ester-substituted organic diamine intermediate, will be employed. The tertiary amine product of this second stage reaction exhibits an N-substituted butenedioic acid residue, i.e., —CO—CH=CH—COOH, in addition to the maleate ester substituent; and this second stage product will be referred to herein as a maleic anhydride/ maleate ester-substituted organic amine. (See Formula IV, supra.)

Reaction of the maleic anhydride/maleate ester organic amine to obtain the complex N-hydroxy-substituted maleimide compounds of this invention may be accomplished by contacting the maleic anhydride/maleate ester-substituted organic amine with hydroxylamine, i.e., $H_2NOH$, or a salt thereof. Preferably, hydroxylamine hydrochloride will be used. Any amount of hydroxylamine may be employed which is effective to react with the maleate ester or vinylene moieties of the maleic anhydride/maleate ester organic polyamine to obtain an effective proportion of N-hydroxy or hydroxylamino substituent groups. Preferably, at least approximately 2 amine equivalents of the hydroxylamine compound will be used. Thus, where organic diamine starting materials are used, it is preferred that about 3-6 moles of hydroxylamine per mole of maleic anhydride/maleate ester-substituted organic diamine be used, and most preferably, about 3.5-4.5 moles hydroxylamine per mole of diamine intermediate will be used.

Where a salt of hydroxylamine is used, the reaction will normally be carried out in the presence of about 1-5 moles (per mole of hydroxylamine compound) of a basic agent, preferably an organic base such as sodium ethoxide, pyridine, triethylamine or quinoline.

The product may be isolated in any one of a number of known ways. For example, the product can be isolated by precipitation from a non-solvent, such as absolute ethanol, and the precipitate filtered, washed and dried under vacuum to give the N-hydroxy maleimide product. These hydroxylamine reaction products, which will be referred to generally as the N-hydroxyimide compounds of the present invention, exhibit N-substituents of a cyclic N-hydroxymaleimide and a 2- or 3-hydroxylamino butanedioic acid residue, i.e., either a —CO—C(NHOH)—CH$_2$—COOH substituent or a —CO—CH$_2$—C(NHOH)—COOH substituent, depending on the precise nature of the hydroxylamine reaction at the unsaturated site.

The N-hydroxyimide compounds are generally soluble in polar solvents, such as dilute sodium hydroxide, ammonium hydroxide or other bases, dimethylsulphoxide, N,N-dimethylformamide, N,N-dimethylacetamide. They are generally insoluble in non-polar solvents, such as hexane, ethyl ether, alcohols, dilute hydrochloric acid, dilute acetic acid.

In the presence of base, the N-hydroxyimide compounds undergo a ring-opening reaction so that the cyclic N-hydroxyimide moiety is cleaved to obtain a difunctional carboxy hydroxamic acid moiety. The structure of the carboxy hydroxamic acid groups with respect to the polyamine nitrogens will be —CH(COOH)—CH$_2$—CO—NHOH or —CH(—CO—N-HOH)—CH$_2$—COOH, depending upon the precise cleavage of the N-hydroxyimide ring during the hydrolysis reaction. Where the reaction takes place in a solution of an alkali metal hydroxide, such as NaOH, alkali metal salts of the carboxy hydroxamic acid products are also contemplated.

The N-hydroxyimide compounds and the carboxy hydroxamic acid derivatives are active transition metal ion chelating agents and are advantageously included in a detergent composition to boost stain-removal properties, in accordance with the present invention. A detergent composition of this invention will contain at least one detersive surfactant. Such surfactants will be present in amounts usually encountered in detergent compositions, e.g., from about 1% to about 50% by weight, preferably about 5% to about 25% by weight for fabric-washing detergents, and most preferably from about 10% to about 20% by weight based on the total weight of the detergent composition. The surfactants may be anionic, nonionic, cationic or amphoteric, and mixtures of different detersive surfactants may be used. Non-limiting examples of suitable detersive surfactants include:

(a) Anionic surfactants: soaps, i.e., alkali metal (preferably sodium or potassium) salts of long-chain fatty acids containing from 8 to 20 carbon atoms, such as lauric, myristic, oleic, palmitic, capric, caprylic, and stearic acids, used singly or in mixtures of differing chain lengths; alkali metal salts of organic sulphuric reaction products having long hydrocarbon chains of about 8 to about 20 carbon atoms and a radical selected from the group consisting of sulphonic acid and sulfuric acid ester radicals, such as sodium or potassium alkyl sulphates, preferably those obtained by sulphating higher (C$_8$–C$_{18}$) alcohols; sodium or potassium alkyl benzene-sulphonates in which the alkyl group contains from about 9 to about 20 carbon atoms, such as sodium linear alkyl (C$_{10}$–C$_{15}$) secondary benzenesulphonate, 2-phenyl-dodecanesulphonate, 2-phenyl-octadecanesulphonate and 3-phenyl-dodecanesulphonate; alkali metal (preferably sodium) olefin sulphonates, i.e., the mixture of detersive surfactants obtained from sulphonation of C$_8$–C$_{22}$ olefins, preferably straight-chain alpha-olefins; sodium alkyl glyceryl ether sulphonates, including ethers of higher alcohols derived from tallow coconut oil and synthetic alcohols derived from petroleum; sodium coconut oil fatty acid monoglyceride sulphates and sulphonates; sodium or potassium salts of sulfur acid esters of the reaction between higher fatty alcohols (e.g., tallow or coconut oil alcohols) and ethylene oxide; the esterification products of fatty acids with isethionic acid, neutralized with sodium hydroxide; and sodium or potassium salts of fatty acid amides of methyl taurine.

(b) Nonionic synthetic detersive surfactants: compounds formed by condensing ethylene oxide with a hydrophobic base formed by the condensation of propylene oxide with propylene glycol; the polyethylene oxide condensates of alkyl-phenols, e.g., the condensation products of alkyl-phenols, having an alkyl group containing from about 6 to 12 carbon atoms in either a straight or branched chain, with ethylene oxide, said ethylene oxide being present in amounts equal to 5 to 25 moles of ethylene oxide per mole of alkyl-phenols (the alkyl substituent in such compounds may be derived from polymerised propylene, diisobutylene, octene, dodecene, or nonene, for example); compounds derived from the condensation of ethylene oxide with the product resulting from the reaction of propylene oxide and ethylenediamine, such as compounds containing from about 40% to about 80% polyoxyethylene by weight and having a molecular weight of from about 5,000 to about 11,000 resulting from the reaction of ethylene oxide groups with a hydrophobic base constituted of the reaction product of ethylenediamine and excess propylene oxide, said hydrophobic base having a molecular weight of the order of 2,500 to 3,000; the condensation product of aliphatic alcohols having from 8 to 18 carbon atoms, in either straight chain or branched chain configuration, with ethylene oxide, e.g., a coconut alcohol-ethylene oxide condensate having from 6 to 30 moles of ethylene oxide per mole of coconut alcohol, the coconut alcohol fraction having from 10 to 14 carbon atoms; long chain tertiary amine oxides corresponding to the following general formula, $R^1R^2R^3N=O$, wherein $R^1$ is an alkyl radical of from about 8 to 18 carbon atoms and $R^2$ and $R^3$ are each methyl, ethyl or hydroxyethyl radicals, such as dimethyl-dodecylamine oxide, dimethyloctylamine oxide, dimethyldecylamine oxide, diethyltetradecylamine oxide and dimethylhexadecylamine oxide, N-bis (hydroxyethyl)dodecylamine oxide; long chain tertiary phosphine oxides corresponding to the following formula $R^4R^5R^6P=O$, wherein $R^4$ is an alkyl, alkenyl or monohydroxyalkyl radical of 10 to 18 carbon atoms and $R^5$ and $R^6$ are each alkyl or monohydroxyalkyl groups containing from 1 to 3 carbon atoms, such as dimethyldodecylphosphine oxide, dimethyltetradecylphosphine oxide, ethylmethyltetradecylphosphine oxide, cetyldimethylphosphine oxide, dimethylstearylphosphine oxide, cetylethylpropylphosphine oxide, diethyldodecylphosphine oxide, diethyltetradecylphosphine oxide, bis(hydroxymethyl)dodecylphosphine oxide, bis(2-hydroxy-ethyl)dodecylphosphine oxide, 2-hydroxypropylmethyltetradecyl-phosphine oxide, dimethyloleylphosphine oxide, and dimethyl-2-hydroxydodecylphosphine oxide; and dialkyl sulphoxides corresponding to the following formula, $R^7R^8S=O$, wherein $R^7$ is an alkyl, alkenyl, beta- or gamma-monohydroxyalkyl radical or an alkyl or beta- or gamma-monohydroxyoxyalkyl radical containing one or two other oxygen atoms in the chain, the $R^7$ groups ranging from 10 to 18 carbon atoms in chain length, and wherein $R^8$ is methyl, ethyl or alkylol, such as dodecyl methyl sulphoxide, tetradecyl methyl sulphoxide, 3-hydroxy-tridecyl methyl sulphoxide, 2-hydroxydodecyl methyl sulphoxide, 3-hydroxy-4-decyloxybutyl methyl sulphoxide, 3-hydroxy-4-dodecyloxybutyl methyl sulphoxide, 2-hydroxy-3-decyloxypropyl methyl sulphoxide, 2-hydroxy-3-dodecyloxypropyl methyl sulphoxide, dodecyl ethyl sulphoxide, 2-hydroxydodecyl ethyl sulphoxide, dodecyl-2-hydroxy ethyl sulphoxide.

(c) Ampholytic synthetic surfactants: derivatives of aliphatic secondary and tertiary amines, in which the aliphatic radical may be straight chain or branched chain and wherein one of the aliphatic substituents contains from about 8 to 18 carbon atoms and one contains an anionic water solubilizing group, such as sodium-3-dodecylamino-propionate, sodium-3-dodecylaminopropanesulphonate and sodium N-2-hydroxydodecyl-N-methyltaurate.

(d) Zwitterionic synthetic surfactants: derivatives of aliphatic quaternary ammonium compounds, sulphonium compounds and phosphonium compounds in which the aliphatic radical may be straight or branched chain and wherein one of the aliphatic substituents contains from about 8 to 18 carbon atoms and one contains an anionic water solubilizing group, such as 3-(N,N-dimethyl-N-hexadecylammonio)propane-1-sulphonate, 3-(N,N-dimethyl-N-hexadecylammonio)-2-hydroxypropane-1-sulphonate, 3-(dodecylmethylsulphonium) propane sulphonate, and 3-(cetyl-methylphosphonium) ethane sulphonate.

The detergent compositions of the present invention will contain, besides one or more detersive surfactants, about 3% to about 12% by weight of the composition, preferably about 6% by weight, of the N-hydroxyimide and/or carboxy hydroxamic acid detergent compounds described above. The complex, alternating structure of the multifunctional compounds of this invention may enhance their metal chelating effectiveness by providing a variety of spacings between functional chelating groups, which, in turn, allows the compounds to sequester a wider variety of cations.

In addition to the surfactants and the N-hydroxyimide detergent additives, the detergent composition may also contain conventional detergent builders such as condensed phosphates, trisodium nitrilotriacetate (NTA), sodium carbonate, zeolites, sodium silicates, etc., and organic polymers such as polyacrylates, polymaleates and polymethacrylates. See, e.g., U.S. Pat. Nos. 3,393,150, 3,666,664, 3,707,502, 3,839,215 and 4,067,816, incorporated herein by reference. The combined detergent builders will make up from about 10% to about 50% by weight of the detergent composition. In addition to the essential detersive surfactants and detergent additives, a detergent composition of the invention may also include such conventional ingredients as lather boosters (e.g., alkanolamides), fillers, antiredeposition agents, fluorescers, pigments, germicides, scents, and enzymes.

A detergent composition according to the invention can be prepared by any conventional manufacturing technique used for preparing detergent compositions, such as slurry making and spray-drying, and the detergent can take anyone of the common physical forms associated with detergents, such as powders, flakes, granules, noodles, cakes, bars and liquids.

The invention is further illustrated by the following examples, which should not be contrued as limiting the scope of the invention.

EXAMPLE 1

72 g (0.50 mole) of dimethyl maleate were added to a solution of 25 g (0.215 mole) hexamethylenediamine in 150 ml of toluene. An exotherm resulted in which the reaction mixture reached 70° C. After the exotherm subsided, the reaction mixture was refluxed for two hours. The reaction mixture was cooled and then 49 g (0.50 mole) of maleic anhydride were added. Another exotherm resulted.

After the exotherm had subsided, the reaction mixture was refluxed for two hours and then cooled. The toluene was removed in a rotary evaporator at reduced pressure. Excess dimethyl maleate and maleic anhydride were removed with a Kugelrohr still at 100° C. at 1 mm Hg pressure, yielding 121.3 g of a yellowish thick oil which later solidified into a glass.

Infrared (IR) and nuclear magnetic resonance (NMR) spectrometry confirmed the presence of both the expected N-substituents, resulting from cis-dimethyl maleate and maleic anhydride (having intact $-CH=CH-$ moiety) residues.

An ethanolic solution of hydroxylamine was prepared by adding 15 g (0.65 mole) of sodium to 300 ml absolute ethanol. This solution was then combined with a solution of 22 g (0.317 mole) of hydroxylamine hydrochloride in 350 ml absolute ethanol at 40° C. The reaction mixture was cooled to 0° C. and filtered.

50 g (0.083 mole) of the maleate ester/maleic anhydride intermediate were added in 50 ml of ethanol to the ethanolic solution of hydroxylamine. The reaction mixture was allowed to stand at room temperature for two days, with formation of a white precipitate.

400 ml of hexane were added to the reaction mixture, which was then filtered. The white solid obtained was dissolved in 300 ml of water and the pH adjusted to 8.0 with concentrated HCl. The solution was then freeze dried to give 56.9 g of an orange solid.

IR, NMR and ultraviolet spectra were obtained, indicating an N-hydroxyimide/2- or 3-hydroxylamino butanedioic acid-substituted product of about 80% purity.

EXAMPLE 2

The performance of the N-hydroxyimide compound Example 1 as a fabric-washing detergent additive was examined in a tea stain removal test:

Swatches of white cotton cloth were boiled in very strong tea (10 tea bags/1 liter dionized water), brewed 10 min.) for 15 minutes. The tea solution and swatches were removed from the heat and cooled to 115° F. with continued stirring. The swatches were thereafter wrung and air dried between paper towels.

Deionized water was heated to 40° C. and 100 mg of CaCl$_2$ were added per each liter of water, followed by 1.5 g per liter of water of a commercial fabric-washing detergent (Tide ®; Procter & Gamble).

To 1-liter aliquots of this detergent solution were added 100 mg of the detergent additives to be tested, which were stirred until dissolved. The wash solutions were maintained at about 35° C. and a stirring speed of 100 rpm. The pH was adjusted to 10 if necessary with sulfuric acid or sodium hydroxide. Tea stained swatches of cloth were added to each test solution and stirred rapidly for 10 minutes, after which the solution was poured off and the swatches squeezed out and rinsed for 2 minutes in deionized water containing the same proportion of CaCl$_2$. The swatches were then air dried overnight and compared against a control and a commercial detergent additive.

The detergent additives of Example 1 was compared against a control (no additive) and a commercial detergent additive (Dequest ® 2041; Monsanto). After the complete wash cycle, the swatches of the control solution appeared darkest, and the comparison sample and the sample using the detergent additive according to the invention appeared visibly lighter.

It will be understood that the foregoing description of the invention is susceptible to modifications, changes and adaptations, all of which are intended to be comprehended within the meaning and range of equivalents of the appended claims. For instance, though the foregoing description is directed to the use of the N-hydroxyimide compounds and their carboxy hydroxamic acid derivatives in detergent systems, they will also find application in boiler water systems and other scale prevention uses, polymerization intermediates, and other embodiments where strong metal ion chelation is required.

I claim:

1. A compound having the formula

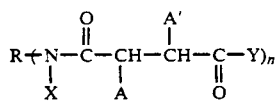

wherein
X is

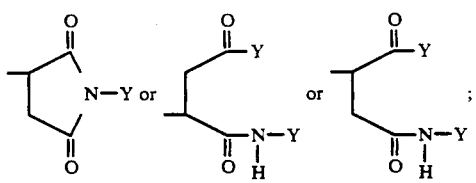

Y is hydroxyl or $-O^-M^+$, where $M^+$ is an alkali metal or ammonium cation;
one of A and A' is hydrogen and the other is

R is an organic radical of 2–20 carbon atoms; and
n is an integer equal to the valency of R.

2. A compound as defined in claim 1, wherein R is divalent radical and n is 2.

3. A compound as defined in claim 2, wherein R is straight-chain alkylene having 5 to 20 carbon atoms.

4. A compound as defined in claim 3, having the formula

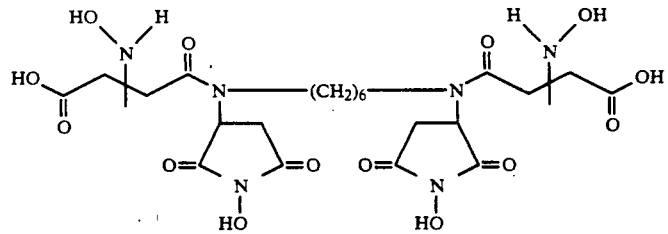

or

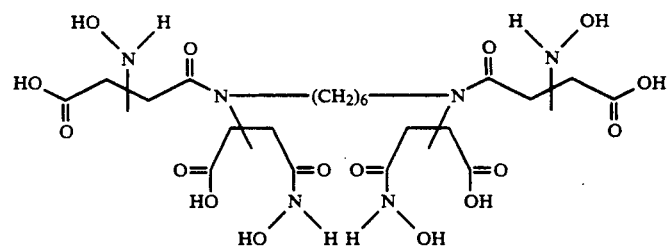

or alkali metal or ammonium salts thereof.

5. A compound as defined in claim 1, wherein R is a mono-valent organic radical and n is 1.

6. A compound as defined in claim 5, wherein R is straight-chain alkyl having 12 to 20 carbon atoms.

7. A compound as defined in claim 6, having the following formula:

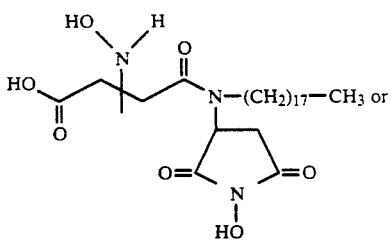

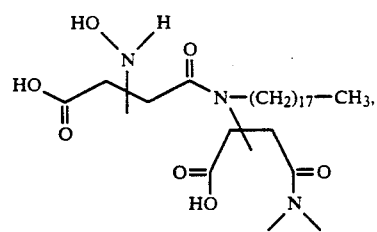

or alkali metal or ammonium salts thereof.

8. A detergent composition comprising one or more detersive surfactants and one or more detergent additives consisting essentially of N-hydroxyimide compounds of the formula

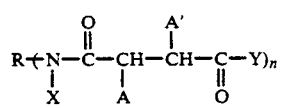

wherein
X is

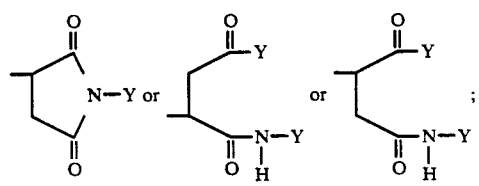

Y is hydroxyl or —O⁻M⁺, where M⁺ is an alkali metal or ammonium cation;
one of A and A' is hydrogen and the other is

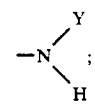

R is an organic radical of 2-20 carbon atoms; and n is an integer equal to the valency of R.

9. A detergent composition as defined in claim 8, wherein R is a divalent organic radical and n is 2.

10. A detergent composition as defined in claim 9, wherein R is straight chain alkylene having at least 5 carbon atoms.

11. A detergent composition as defined in claim 10, having the formula

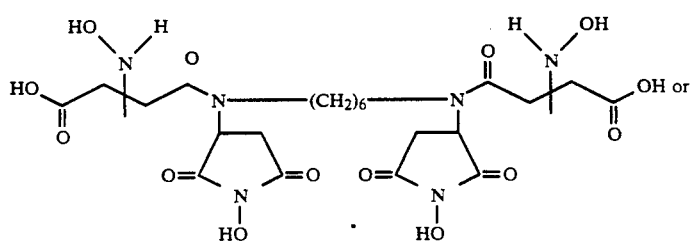

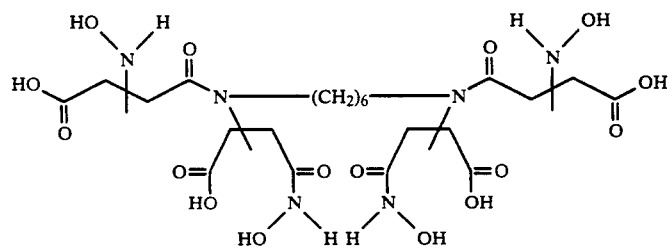

or alkali metal or ammonium salts thereof.

12. A detergent composition as defined in claim 8, wherein R is a mono-valent organic radical and n is 1.

13. A detergent composition as defined in claim 12, wherein R is straight-chain alkyl having 12 to 20 carbon atoms.

14. A detergent composition as defined in claim 13, having the following formula:

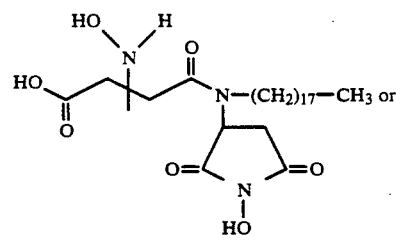

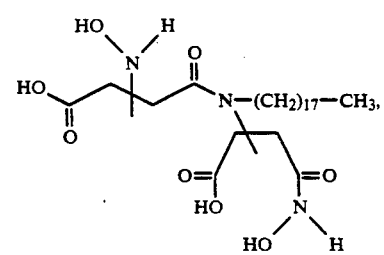

or alkali metal or ammonium salts thereof.

15. A detergent composition as defined in claim 8, wherein the detersive surfactant is an anionic surfactant, a nonionic synthetic surfactant, or a combination of anionic and nonionic surfactants.

16. A detergent composition as defined in claim 8, wherein said detersive surfactants comprise about 5% to about 25% by weight of the detergent composition, and said detergent additives comprise about 3% to about 12% by weight of the detergent composition.

17. A detergent composition as defined in claim 8, which also contains ingredients selected from the group consisting of lather boosters, fillers, antiredeposition agents, fluorescers, pigments, germicides, scents, enzymes and other detergent builders.

18. A detergent composition as defined in claim 8, also including detergent builders in amounts from about 10% to about 50% by weight of the detergent composition.

* * * * *